United States Patent [19]
Reddy

[11] Patent Number: 5,337,736
[45] Date of Patent: Aug. 16, 1994

[54] METHOD OF USING A LAPAROSCOPIC RETRACTOR

[76] Inventor: Pratap K. Reddy, 5610 Hyland Greens Dr., Bloomington, Minn. 55437

[21] Appl. No.: 953,940

[22] Filed: Sep. 30, 1992

[51] Int. Cl.⁵ .............................................. A61B 17/00
[52] U.S. Cl. ...................................... 128/20; 128/898; 600/37; 606/225; 606/191
[58] Field of Search ................. 128/20, 3, 898, 897; 602/4; 600/37; 606/151, 158, 138, 148, 145, 213, 222, 224, 225, 228, 1, 191

[56] References Cited

U.S. PATENT DOCUMENTS

| | | |
|---|---|---|
| 2,143,910 | 1/1939 | Didusch . |
| 3,665,926 | 5/1972 | Flores . |
| 3,871,379 | 3/1975 | Clarke . |
| 3,877,434 | 4/1975 | Ferguson et al. . |
| 3,983,863 | 10/1976 | Janke et al. . |
| 4,217,890 | 8/1980 | Owens . |
| 4,271,828 | 6/1981 | Angelchik ............. 600/37 |
| 4,517,965 | 5/1985 | Ellison .................. 128/20 |
| 4,744,363 | 5/1988 | Hasson . |
| 4,979,956 | 12/1990 | Silvestrini ............. 623/13 |
| 5,006,106 | 4/1991 | Angelchik . |
| 5,078,721 | 1/1992 | McKeating ............ 606/139 |
| 5,106,369 | 4/1992 | Christmas ............. 128/20 X |
| 5,183,033 | 2/1993 | Wilk ...................... 128/20 |
| 5,222,508 | 6/1993 | Contarini .............. 128/898 |
| 5,222,976 | 6/1993 | Yoon .................... 606/228 X |
| 5,226,429 | 7/1993 | Kuzmak ................ 128/898 |

OTHER PUBLICATIONS

W. Schuessler and T. G. Vancaillie, Techniques in Endosurgery, Laparoscopic Lymphadenectomy, ETHICON publicaiton No. ENDO35.

*Primary Examiner*—Richard J. Apley
*Assistant Examiner*—Donna L. Mareglio
*Attorney, Agent, or Firm*—Moore & Hansen

[57] ABSTRACT

A retraction method and apparatus therefor are useful in laparoscopic surgery in a body cavity, for moving an internal organ or vessel which interferes with the surgery to an out-of-the-way displaced position and maintaining it there apart from a laparoscopic port. In this method, a sling having attached suture material is inserted into the body cavity through a laparoscopic port and manipulated about the organ/vessel to be moved, by a retractor and/or forceps. A small needle hole is then punctured into the cavity, a narrow retrieval instrument is inserted through the needle hole to retrieve the ends of several suture leads attached to the sling, and to retract them from the body cavity to move the interfering organ or vessel to a non-interfering position. The suture leads may be clamped or tied off outside the body. Tools useful with the method include a sling, a retrieval instrument and a J-hook passer-retractor.

13 Claims, 5 Drawing Sheets

METHOD OF USING A LAPAROSCOPIC RETRACTOR

BACKGROUND OF THE INVENTION

This invention relates generally to surgical methods and apparatus. More particularly, this invention pertains to methods and apparatus for laparoscopic endosurgical retraction.

Traditional endosurgery in the chest or abdominal cavity is performed by large instruments through large incisions. Organs and vessels, e.g. intestines or bowels, must often be pulled or pushed aside to provide access to the particular target area of surgery. Conventionally, large retractors and retraction clamps are used for holding the interfering organ or vessel out of the way during the surgical operations; such procedures require large incisions with accompanying intense trauma.

In recently developed laparoscopic surgery, one or more small sealable ports or trocars are established through the body cavity wall. These ports may vary in diameter, typical port sizes being about 5 and 11 mm in diameter. Standard retractors are too large to be inserted through laparoscopic ports, so special miniature instruments must be used. All of the instruments are used through the sealable laparoscopic ports. Thus, the miniature laparoscopic instruments have handles which project from the port for external manipulation. The port is designed to seal against excessive loss of insufflation gas, the latter typically injected into the cavity to expand it.

Laparoscopic surgery offers great promise for reducing patient trauma, pain, hospitalization time, cosmetic disfigurement and expense typical of much of traditional full-scale laparotomy.

One of the limitations with laparoscopic surgical procedures has been the difficulty in moving interfering organs and vessels away from the surgical target area, and maintaining them in a non-interfering location. At present, rigid instruments passing through the laparoscopic port are used in some cases to retract the interfering organ. However, these instruments must often span a considerable distance across the cavity to pull or push the organ or vessel aside, making such manipulation difficult. In addition, these instruments themselves may converge in the operating area, crowding the target surgical area and increasing the difficulty of access. These instruments also monopolize laparoscopic ports which may more advantageously be used for passage of other surgical instruments. Furthermore, it may be necessary to increase the size of the surgical team to continuously maintain traction on the organ or vessel to maintain it in the desired displaced position during the surgical operation.

A method and apparatus are needed for better retraction and exposure during laparoscopic surgery within a body cavity, to enable precise positioning of organs or vessels, to reduce the operating time and the recovery period, to reduce the cost of surgery, and to expand the applicability of laparoscopic surgical techniques.

BRIEF SUMMARY OF THE INVENTION

This invention provides a method and apparatus, in laparoscopic procedures, for translating an internal body member from an original position to a displaced position within a body cavity such as a chest or abdominal cavity, and maintaining the body member in the displaced position.

The apparatus of the invention comprises three types of tools useful in the method, i.e. a miniature sling with attached leads for retraction, a J-hook tool for passing the sling about an organ to be moved, and a retrieval instrument for drawing the sling leads.

The method of the invention is particularly useful for moving an organ or vessel which is located in a position interfering with a desired surgical procedure. It is also useful in moving an organ or vessel to a more favorable position or attitude for surgery or other process applied to the translated organ/vessel itself. The method may be advantageously applied in any laparoscopic surgery.

Preliminary to the application of this invention, the body cavity is insufflated with gas to an elevated pressure, and one or more laparoscopic ports or trocars are established through the cavity wall into the cavity itself. At least one laparoscopic port is sufficiently large, e.g. about 10-11 mm diameter, for introduction of a sling, ligature, or suture material into the cavity. The sling, together with attached leads, e.g. suture material, comprises a retracting device which is wrapped around the translatable organ/vessel by one or more instruments, e.g. forceps, inserted through a laparoscopic port. The suture material or other lead material is then drawn by laparoscopic instrument(s) to proximate the inner side of the cavity wall near the desired displacement position.

A small "needle hole" aperture is then formed in the cavity wall near the desired displacement position. The "needle hole" is sufficiently small to prevent any significant loss of insufflation pressure. A slender acuminate retrieval instrument is inserted through the "needle hole" aperture to grasp the lead material and retract it through the "needle hole" to exterior the cavity wall. The organ or vessel is thus drawn from the original position to the restrained displacement position. The ends of the lead material are then fixed and maintained by tying off and/or by clamping with clamps or other means to immobilize the organ or vessel in the desired displaced position.

The needle hole is typically on the order of about 1-8 mm in diameter and preferably in the range of 1-5 mm. A particular retrieval instrument which is adapted to form the required needle hole is disclosed herein.

Following the surgical procedure, the displaced organ or vessel may be returned to its original or another position by releasing the sutures through the "needle hole" and removing the sling or ligature and/or sutures e.g. through a laparoscopy port.

This invention encompasses miniaturized tools particularly applicable to this procedure, including a J-hook passer tool operable through a laparoscopy port and a sling passable through a laparoscopic port when folded or rolled. The sling is operable to embrace an internal body member and be moved to a displaced position by lines or leads such as suture filaments. A further tool of the invention comprises a suture retrieval needle operable through a self-made "needle hole" to grasp and retract leads attached to the sling for drawing the organ/vessel from its original position to a displaced position.

The methods and apparatus of this invention, as well as the advantages thereof, will be readily understood from the following description in conjunction with the accompanying figures of the drawings, wherein like

DESCRIPTION OF THE PREFERRED EMBODIMENTS

Figure 1:
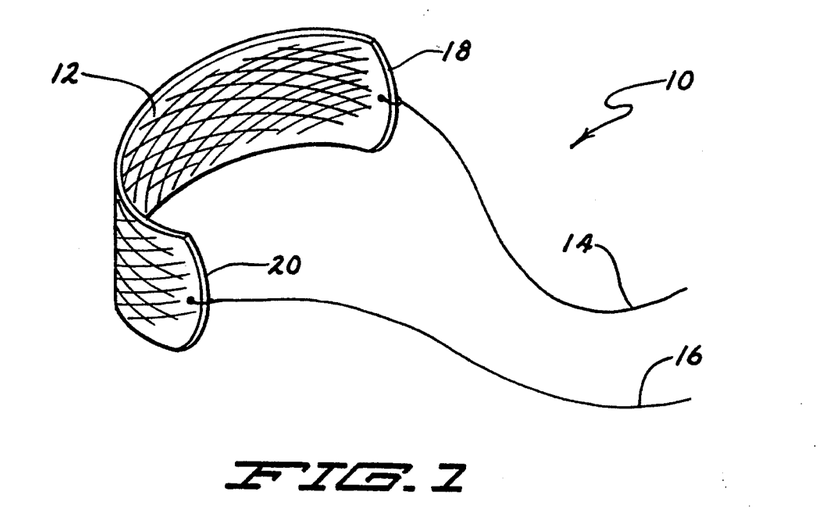
FIG. 1 is a general view of a sling of the invention.

With reference to the drawings, and particularly to FIG. 1, a harness or sling 10 of the invention is shown as comprising a web or membrane 12 with one or more, e.g. two lines or leads 14, 16 attached, one on each end 18, 20 of the sling 10. The web 12 is configured to embrace an internal body member such as a vessel or organ.

The web or membrane 12 of sling 10 comprises a material type and size which may be folded, rolled tip or otherwise compacted to a size which may be passed through a trocar port for use in laparoscopic procedures. The web may be formed of any biocompatible material which has the necessary strength and flexibility. Typical materials of construction include latex rubber, silastic, silicone rubber, urethane, fabric comprising natural or synthetic materials, and other soft plastics, or other materials. A material form commonly known as umbilical tape, and similar materials may also be advantageously used in a variety of applications. Various materials may be combined to provide the desired web properties.

The web 12 may have a solid impervious surface. Alternatively, the web may be comprised of a material formed into a mesh with openings therein. An example of such a material is a latex coated open weave material.

For translating and holding some organs and vessels in a displaced position, the texture of the web may be important. For example, the texture of very smooth Teflon will be much different from a smooth robber surface, and both differ from a stippled surface of rubber which has a high degree of "clinginess".

The web 12 may be any shape or size, provided the resulting sling will pass through the trocar and the size is adequate for retraction of the particular internal body member. Typically, the web is generally oblong with a short dimension of about 2-30 mm and a long dimension of about 10-100 mm or more. The particular size, shape, surface texture and material best suited for a particular application is generally based on the size and fragility of the organ/vessel to be translated, as determined by good judgement and experience.

The lead or leads are preferably attached to the web 12 prior to introducing the sling into the body cavity, or may alternatively be attached intracorporeally.

The leads 14, 16 may comprise monofilament or multifilament suture strands or ligaments, or other thin cord, strip or ribbon material which may be passed through a small "needle hole". The material is chosen to exhibit a limited degree of elasticity as desired for safely moving the selected internal organ or vessel the required displacement distance and maintaining the organ or vessel in the displaced position.

In FIG. 1, the sling 10 is shown with a web 12 formed of a generally oblong piece of material, whose length is about 5 times its width. A simple lead 14 of suture material is joined to end 18 of the web, and one end of lead 16 is joined to a web end 20.

The number and types of leads may be varied to fit the particular application. The shape as well as the ratio of web length to web width may also be widely varied, as desired.

Figure 2:
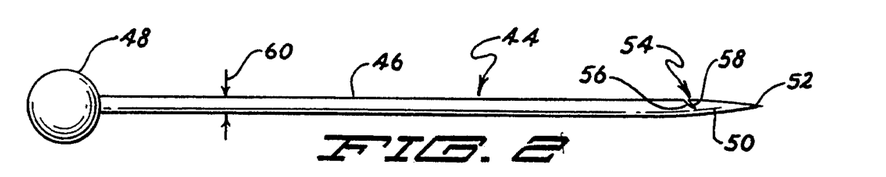
FIG. 2 is a side view of a retriever tool of the invention.

In FIG. 2, a sub-laparoscopic retrieval tool 44 useful in this method is illustrated. The tool 44 comprises a thin acuminate shaft 46 having a first end which is an enlarged handle portion 48 for manipulating the tool 44 and preventing it from totally entering a body cavity. The opposite end 50 is tapered to a sharp point 52, and contains at least one lead retrieving slit 54. The sharp point 52 enables the shaft 46 to pierce through a wall of the body cavity, forming a small "needle hole" through which the shaft 46 may be further inserted to retrieve one or more leads 14, 16 of sling 10 in slit 54. The sides 56, 58 of slit 54 are configured to converge inwardly so that as a lead or leads 14 and/or 16 are forced into the slit 54, the leads become wedged in the slit. The retraction force required to fully displace the organ or vessel may be applied to the retriever 44 without fear of slippage between the retriever and the lead or leads.

The retriever tool 44 may have a circular or oval cross-section, or other cross-sectional shape that avoids significant loss of insufflation gas from the body cavity through the needle hole. The shaft portions rearward of point 52, which enter the body, have a maximum diameter 60 of about 1 to 7 mm, and are more typically of about 2-4 mm diameter. The optimal lengths for various surgical procedures fall into the range of about 5-25 cm.

The retriever tool 44 is formed of a rigid material, typically a metal, plastic or other material with sufficient strength to withstand the forces exerted upon it.

The retrieval tool 44, when inserted in the small "needle" hole in the peritoneum is surrounded by flesh which effectively seals the space around the tool. Loss, if any, of insufflation gas to the atmosphere is very low.

The dual usage retriever tool 44 obviates the use of a separate puncturing tool, shortening the surgical procedure. However, the tool 44 may be used simply for retrieving and/or retracting through a needle hole formed by another tool.

Figure 3:
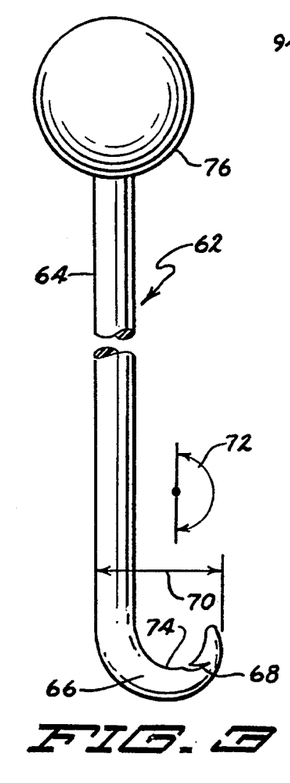
FIG. 3 is an enlarged side view of a J-hook laparoscopic tool of the invention.

FIG. 3 depicts a one-piece J-hook passer or passer-retractor 62 of the invention. This tool is configured for the primary purpose of passing a sling 10 about an internal vessel or organ and passing the leads of the sling to the retriever tool 44. Passer 62 may also be used for pushing or pulling body members.

Passer 62 is shown as a one-piece tool having a straight or slightly bowed elongated shaft portion 64 and a hook portion 66 at one end thereof. The hook portion 66 has one or more lead slots 68 for wedgingly catching one or more leads and passing it or them around the organ or vessel, and then passing the leads to a retriever such as retrieval tool 44. The opposite end of the shaft portion 64 comprises an enlarged handle 76 which is manipulable from exterior the body cavity and prevents complete insertion through a port. The J-hook passer 62 has a maximum overall diameter 70 which enables it to be inserted through a laparoscopic port into a body cavity for the lead passing procedures. The passer 62 may be withdrawn after the leads have been caught by the retriever tool 44, to free the laparoscopic port for other uses.

If desired, the J-hook passer 62 may be used to remove the sling 10 from the body cavity after the displaced organ/vessel has been returned to the permanent position.

As shown in FIG. 3, passer 62 has a rounded end hook portion 66 which is bowed through an angle 72 of about 180 degrees. This high angle eases the task of passing the leads about a relatively narrow vessel. However, the hook portion 66 may be configured to be bowed through a much smaller angle, even as low as about 10-20 degrees. The notch or slot(s) 68 is preferably located on the interior curvature 74 of the hook portion 66.

The passer tool 62 may be formed of metal or plastic or other material; in the plastic construction, it may be considered as a disposable tool.

If desired, the handle portion 76 may have a finely textured surface, increasing the friction to prevent slippage between fingers and handle.

Figures 4, 5:
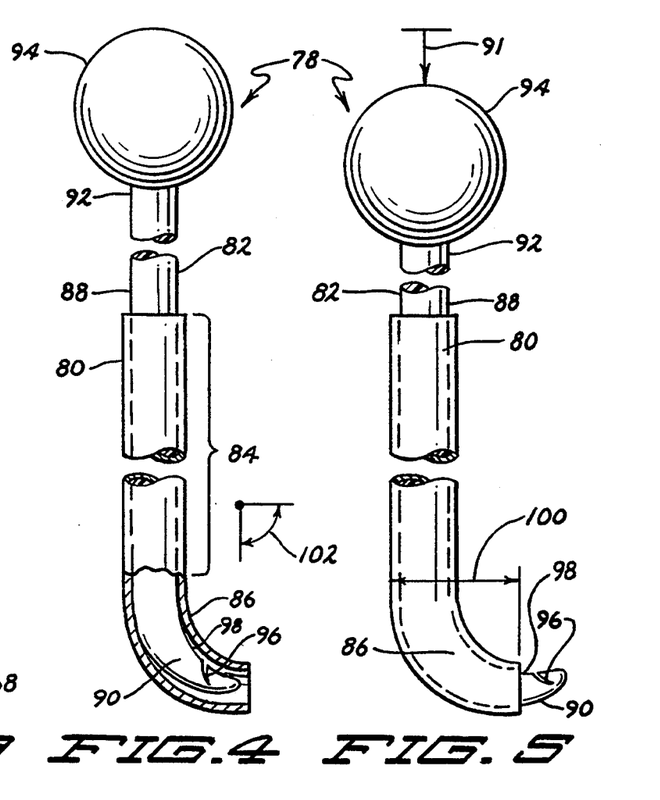
FIG. 4 is an enlarged partially cutaway side view of a two-part J-hook laparoscopic tool of the invention.
FIG. 5 is an enlarged partially cutaway side view of the embodiment of FIG. 4, showing the inner finger in an extended position.

FIGS. 4 and 5 show a two-part J-hook passer tool 78 comprising an outer sheath 80 and an inner finger 82 within the sheath. The sheath has an elongate, generally straight portion 84 and a terminal hook portion 86. The inner finger 82 includes a straight portion 88 and a terminal hook portion 90. The finger 82 is configured to slide lengthwise within the sheath 80. The straight portion 88 of the finger 82 has a terminus 92 which projects from the sheath, and which includes an enlarged handle portion 94 for manually manipulating the finger 82 within the sheath 80. The handle portion 94 may also be mounted to limit the insertion distance of the finger 82 into the sheath 80. The shape of the enlarged handle portion 94 is unimportant so long as it serves the required purposes.

The rounded hook portion 90 of the finger 82 is projectable from the hook portion 86 of the sheath 80. A slit or notch 96 on the inner curvature 98 of the hook portion 90 is configured for hooking and holding one (or more) leads and passing it around a vessel or organ and to a retriever tool. As depicted in FIG. 5, slight pressure 91 on the handle 94 of finger 82, pushing it into the sheath 80, extends the hook portion 90 from the sheath hook portion 86 a short distance, e.g. 1-8 mm for catching leads. When the handle portion 94 of the finger 82 is pulled away from the sheath 80, the hook portion 90 is retracted slightly into the sheath 80, as in FIG.

The sheath 80 may be formed of metal or plastic, and preferably has a wall thickness less than 0.5 mm. The finger 82 is formed of plastic or metal to have the capability to flex when pulled or pushed within the sheath 80. This flexure enables the finger to be projected or withdrawn relative to the sheath, whose hook portion 86 is depicted as passing through an angle 102 of about 90 degrees.

The passer tool 78 is configured to be passed through a laparoscopic port for intracorporeal use. Thus, the maximum width dimension 100 is adapted to pass through the largest laparoscopic port which is to be used in the surgical procedure. For example, the width dimension may be about 10.5 mm for passage and manipulation through a 11 mm trocar port.

Figure 6:
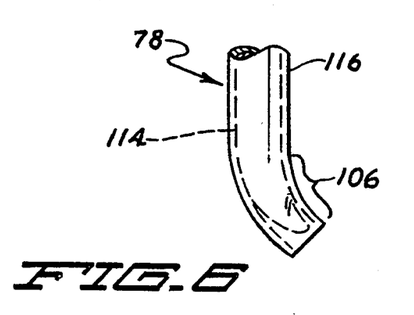
FIG. 6 is an enlarged partially cutaway side view of another embodiment of the two-pan laparoscopic tool of the invention.
Figure 7:
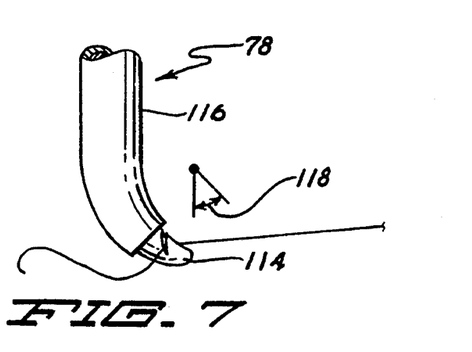
FIG. 7 is an enlarged partially cutaway side view of the embodiment of FIG. 6, showing the inner finger in an extended position.

Another form of the passer tool is shown in FIGS. 6 and 7, in which the hook portion 106 of the sheath 116 is formed to an angle 118 of about 45 degrees, much less than that of passer tool 78 of FIGS. 4 and 5. This allows the finger 114 to be projected much further from the sheath 116 than is possible with passer tool 78 of FIGS. 4 and 5. The angles 102 and 118 may vary from zero to about 90 degrees, depending upon a surgeon's preference in the particular surgical procedure. The lower the angle 102, 118, the larger the sheath 116 and finger 114 may be for passage through a given port size. In other words, when both the sheath diameter and the port size remain unchanged, a lower angle 102 or 118 permits more flexibility and movement of the tool within the port.

The sling, retriever and J-hook tools herein described are useful in a procedure for translating an internal body member such as an organ or vessel from a nondesirable or interfering position to a more desirable displaced position in the body cavity, and maintaining it there. The procedure as applied to moving a vessel such as a vein or artery is illustrated in FIGS. 8-12.

Figure 8:
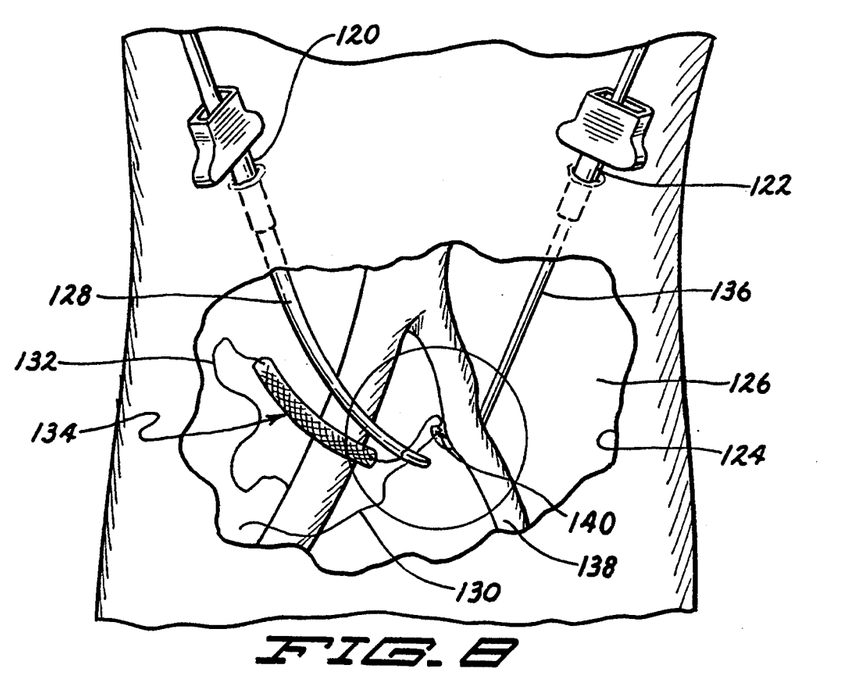
FIG. 8 is a top view of an exemplary abdominal cavity laparoscopy showing the initial steps in moving a vessel to a displaced position by the method and apparatus of the invention.
Figure 9:
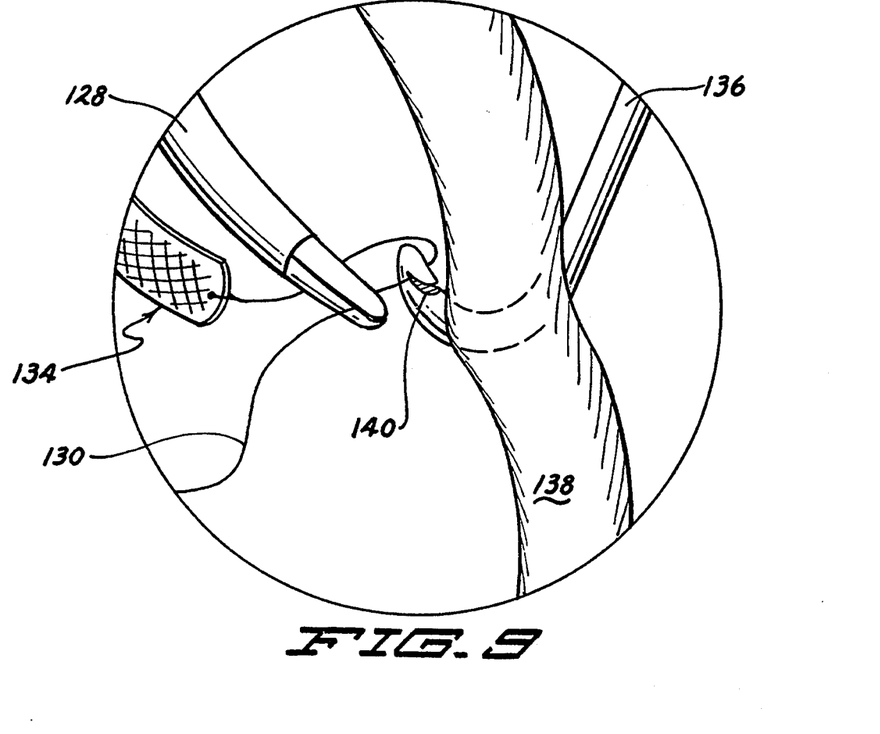
FIG. 9 is an enlarged top view of an exemplary abdominal cavity laparoscopy illustrating steps in moving a vessel to a displaced position by the method and apparatus of the invention.

Turning now to FIGS. 8 and 9, the figures show two laparoscopic or trocar ports 120, 122 established across the abdominal wall 124 from the exterior to the abdominal cavity 126. Typically, the abdominal cavity is insufflated with gas prior to surgery, to expand the working space in the cavity.

A laparoscopic forceps 128 is shown passing through port 120 into the abdominal cavity 126 and gripping one of the leads 130, 132 of an elongate sling 134. Likewise, a one-piece passer tool 136 is shown as having been inserted through second port 122, passed around a representative vessel 138, shown here as the common iliac artery, and has caught lead 130 in its slit or notch 140. The passer tool 136 may be as illustrated in any of FIGS. 3 through 7, or may be a laparoscopic retractor or forceps of some other construction.

Figure 10:
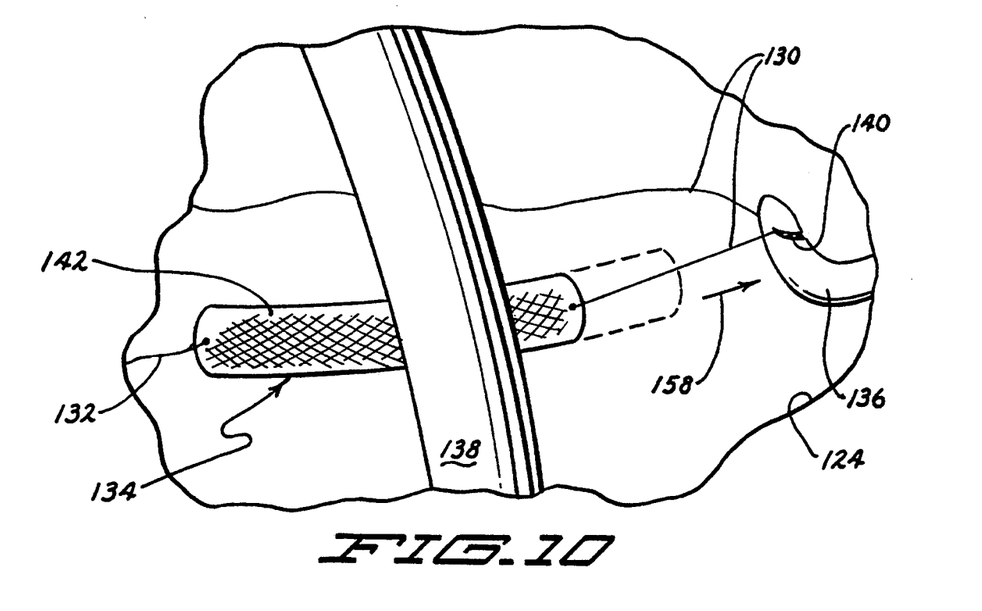
FIG. 10 is a top view of an exemplary abdominal cavity laparoscopy illustrating tertiary steps in moving a vessel to a displaced position by the method and apparatus of the invention.

FIG. 10 illustrates the further step of passing the lead 130 and pulling 158 the membrane or web 142 and the rest of the sling 134 attached thereto about the opposite side of the vessel 138. At this stage, the forceps 128 or other insertion tool is generally no longer needed for this purpose, and may be removed.

Figure 11:
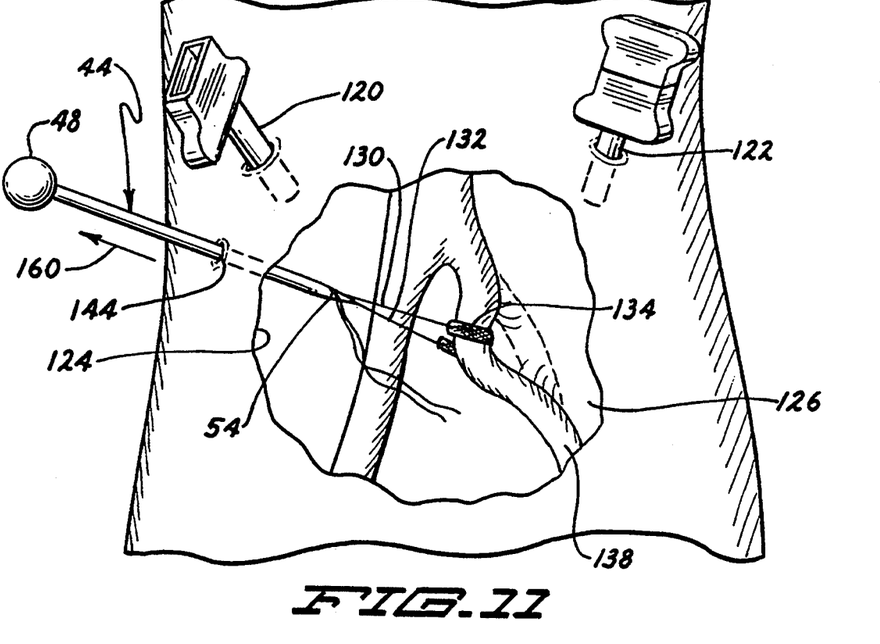
FIG. 11 is a top view of an exemplary abdominal cavity laparoscopy illustrating the retrieval step of the invention.

As shown in FIG. 11, a retriever 44 or similar tool is inserted through a small puncture hole 144, i.e. a "needle hole" through the abdominal wall 124. In this example, the puncture hole 144 is located for drawing the vessel 138 toward the patient's fight side, i.e. in direction 160. When the sling 134 is in place about the vessel 138, the leads 130, 132 are caught by the retrieval tool 44 and drawn outward through the puncture hole 144 in the abdominal wall 124. The passer tool 136 and/or forceps may be withdrawn from the cavity 126 through the trocar ports unless needed for another task within the cavity.

Figure 12:
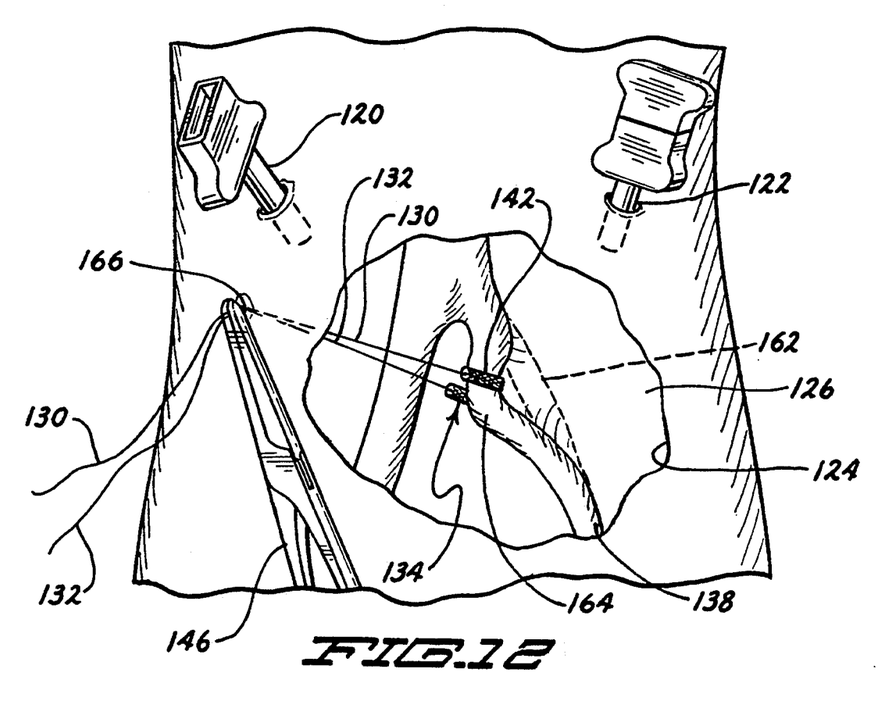
FIG. 12 is a top view of an exemplary abdominal cavity laparoscopy illustrating a further step of the invention.

In FIG. 12, a conventional clamp 146 is shown having clamped the leads 130, 132 outside of the abdominal cavity to retain the vessel 138 in the displaced position 164. Alternatively, the leads may be tied off to fore knot 166 or be held immobile in some other way.

Following laparoscopic surgery, the leads 130, 132 may be snipped or returned to the body cavity 126 so that the vessel 138 is returned to its non-translated or original position 162. The sling 134, including the web 142 and leads 130, 132, is removed through a laparoscopic port such as port 120. Webs 142 of larger sizes may need to be rolled or folded for ready removal.

Figure 13:
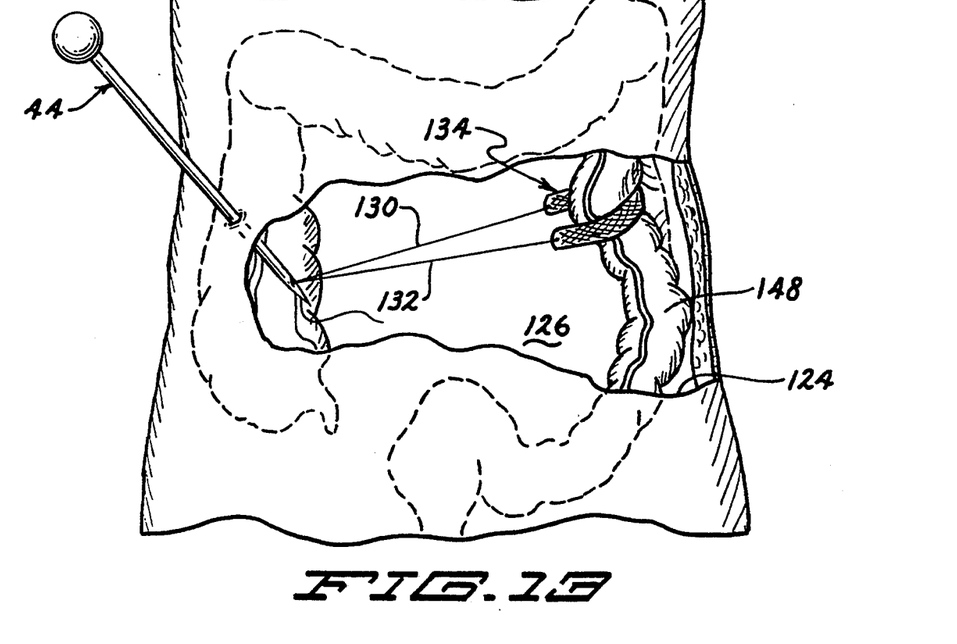
FIG. 13 is a top view of an exemplary abdominal cavity laparoscopy illustrating the retrieval step of the invention as applied to displacement of a body organ.
Figure 14:
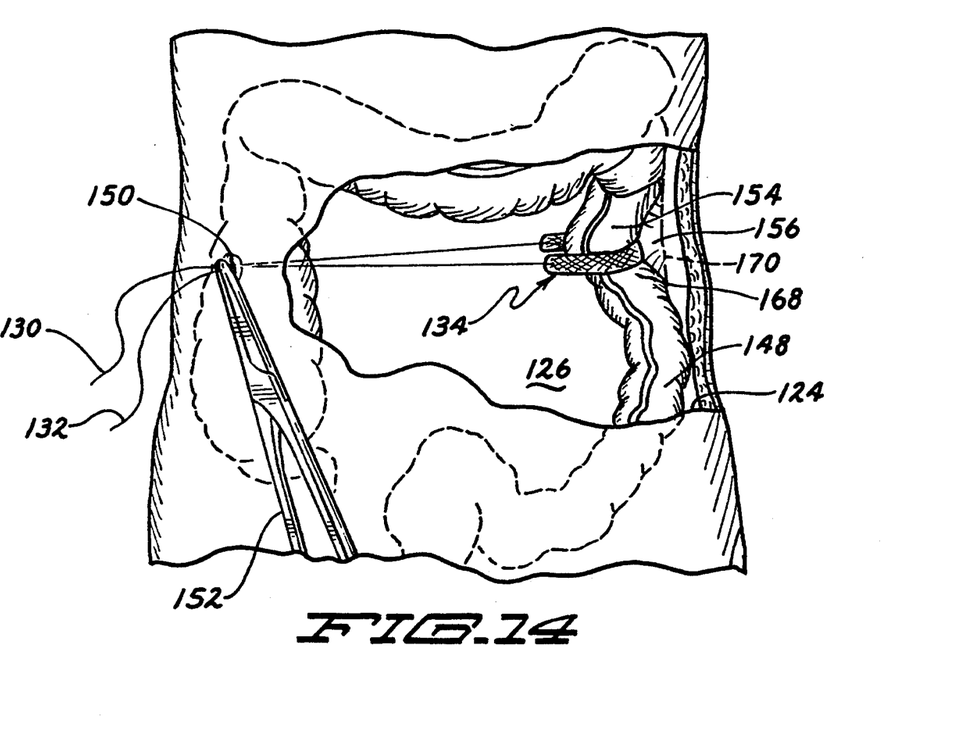
FIG. 14 is a top view of an exemplary abdominal cavity laparoscopy of FIG. 13, illustrating a further step of the invention as applied to displacement of a body organ.

FIGS. 13 and 14 illustrate the body member translation method as applied to the displacement of an organ 148 such as the descending colon. The steps are essentially the same as those described in relation to FIGS. 8–12, and the steps illustrated in FIGS. 13 and 14 correspond more specifically to those of FIGS. 11 and 12, respectively.

In FIG. 13, the step of inserting a retrieval tool 44 into the body cavity 126, and retrieving and retracting the leads 130, 132 of the sling 134 to pull the organ 148 aside for accessing a target surgery area, is shown.

FIG. 14 shows the leads 130, 132 tied off at knot 150 and clamped with a conventional clamp or forceps 152 outside of the abdominal cavity 126. A portion 154 of the descending colon 148 is held in a displaced position 168, away from original position 170, by sling 134 for surgery in an underlying target area 156.

As in the described procedures relating to FIGS. 8–12, the retracting steps may be reversed to return the body member to its original position 162, 170 or another position and remove the sling 134.

Some of the major advantages of this procedure are:
1. an organ or vessel may be moved in any desirable direction and held there during the entire operation period;
2. the leads which continuously maintain the organ or vessel in retraction may be situated away from the site of surgery;
3. the laparoscopic ports are freed for use in the surgical operation rather than in retracting the interfering organ/vessel;
4. a small needle-hole is used rather than a laparoscopic port, minimizing insufflation gas leakage as well as trauma;
5. the procedure may be conducted quickly and accurately; and
6. the target laparoscopic surgery may be performed more accurately and efficiently because of reduced interference from intervening body members.

While the procedure for translating the body member to a displaced position is for the purpose of access to another body member, the procedure is also useful for positioning the translated body member for surgery thereon.

The retraction procedure of the invention is advantageously conducted using the foredescribed tools; alternatively, other laparoscopic and/or sub-laparoscopic tools may be used.

It is anticipated that various changes and modifications may be made in the construction of the apparatus and methods of operation disclosed herein without departing from the spirit and scope of the invention as defined in the following claims.

What is claimed is:

1. A method for applying intracorporeal traction on an internal body member in a body cavity having a laparoscopic trocar inserted thereinto proximate the body member, comprising:
   puncturing the body cavity wall with a sharp instrument to form a needle hole;
   inserting a first end of an acuminate instrument through the needle hole into the body cavity;
   inserting a sling through the trocar into the body cavity;
   placing said sling about the body member within the body cavity;
   extending the acuminate instrument to grasp the sling; and
   drawing the sling with said acuminate instrument to retract the body member toward said needle hole.

2. The method of claim 1, wherein said sharp instrument comprises said acuminate instrument.

3. A method for moving an internal body member to a displaced position in a laparoscopic surgical operation within a body cavity, comprising:
   inserting a miniature sling having attached leads through a laparoscopic port into a body cavity;
   manipulating the sling and leads to embrace a body member;
   inserting a thin acuminate instrument through a needle hole into the body cavity;
   attaching the leads to the thin acuminate instrument; and
   retracting the instrument and leads through the needle hole to move the internal body member to a displaced position.

4. The method of claim 3, comprising the further step of fixing the retracted leads exterior of the needle hole to maintain the body member in the displaced position.

5. A method in laparoscopic procedures for moving an internal body member from an original position to a displaced position within a body cavity and maintaining the member in the displaced position, comprising:
   establishing a plurality of laparoscopic ports across a wall separating the body cavity from external the cavity;
   inserting body member embracing means having lead means attached thereto through a laparoscopic port into the body cavity;
   inserting a laparoscopic retraction tool through a laparoscopic port and manipulating said embracing means about the body member with said retraction tool;
   establishing a needle hole through the wall into the body cavity, said needle hole located for drawing said embracing means and the body member to a displaced position;

inserting retrieval tool means through said needle hole into the cavity and retrieving said lead means therewith;

retracting said retrieval tool means and attached lead means through the needle hole to draw the embracing means and body member to a displaced position; and fixing said lead means external of the body cavity to external fixing means to maintain said embracing means and the body member in said displaced position.

6. The method of claim 5, comprising the further steps of: releasing said lead means from said external fixing means which maintain said embracing means and the body member in said displaced position, and moving the body member to an unrestrained position; and removing said embracing means and lead means from the body cavity.

7. The method of claim 5, wherein said step of retracting said retrieval tool means and attached lead means through the needle hole comprises drawing the embracing means and body member to a displaced position away from the primary surgery target area.

8. The method of claim 5, wherein said step of retracting said retrieval tool means and attached lead means through the needle hole comprises drawing the embracing means and body member to a displaced position for surgical treatment thereof.

9. The method of claim 5, wherein said embracing means comprises a sling having a web formed of a soft, flexible, biocompatible, sterilizable material.

10. The method of claim 9, wherein said lead means comprises suture strands attached to opposed ends of said sling.

11. The method of claim 5, wherein said web is formed of one of silicone rubber, latex rubber, urethane, soft plastic or umbilical tape.

12. The method of claim 5, wherein said body member embracing means is inserted through a first laparoscopic port with a forceps, and said laparoscopic retractor tool is inserted through a second laparoscopic port, and said forceps and said retractor tool are removed from the cavity through said ports after the retriever has retrieved said lead means.

13. The method of claim 5, wherein said lead means are fixed external the cavity by tying off or clamping.

* * * * *